(12) United States Patent
Rangaswamy et al.

(10) Patent No.: US 7,846,699 B2
(45) Date of Patent: Dec. 7, 2010

(54) **PROCESS FOR GIBBERELLIC ACID PRODUCTION WITH "*FUSARIUM MONILIFORME*" STRAINS**

(75) Inventors: Vidhya Rangaswamy, Maharashtra (IN); Guduri Balu, Maharashtra (IN)

(73) Assignee: Reliance Life Sciences Pvt. Ltd., Maharashtra (IN)

( * ) Notice: Subject to any disclaimer, the term of this patent is extended or adjusted under 35 U.S.C. 154(b) by 562 days.

(21) Appl. No.: 11/854,072

(22) Filed: Sep. 12, 2007

(65) Prior Publication Data

US 2008/0085543 A1    Apr. 10, 2008

(30) Foreign Application Priority Data

Sep. 15, 2006   (IN) ...................... 1473/MUM/2006

(51) Int. Cl.
C12P 17/04    (2006.01)
C12N 1/00    (2006.01)
(52) U.S. Cl. .................. 435/126; 435/254.7; 435/256.5
(58) Field of Classification Search ....................... None
See application file for complete search history.

(56) References Cited

U.S. PATENT DOCUMENTS

| | | |
|---|---|---|
| 2,842,051 A | 7/1958 | Brian et al. |
| 2,865,812 A | 12/1958 | Borrow et al. |
| 2,906,670 A | 9/1959 | Borrow et al. |
| 2,906,671 A | 9/1959 | Borrow et al. |
| 2,906,673 A | 9/1959 | Borrow et al. |
| 3,021,261 A | 2/1962 | Bergman et al. |

OTHER PUBLICATIONS

Agosin et al, "Production of gibberellins by soild substrate cultivation of *Gibberella fujikuroi*", edited by Roussous et al, Advances in Solid State Fermentation, 1997, 355-366.
Bandelier et al., "Production of gibberellic acid by fed-batch solid state fermentation in an aseptic pilot-scale reactor", Process Biochemistry, 1997, 32(2):141-145.
Berrios et al., "Spectrophotometric method for determining gibberellic acid in fermentation broths", Biotechnology Letters, 2004, 26: 67-70.
Escamilla et al., "Optimization of gibberellic acid production by immobilized *Gibberella fujikuroi* mycelium in fluidized bioreactors", Journal of Biotechnology, 2000, 76: 147-155.
Ergun et al., "Auxin (Indole-3-acetic acid), Gibberellic acid ($GA_3$), abscisic acid (ABA) and cytokinin (Zeatin) production by some species of Mosses and Lichens", Turk J Bot., 2002, 26: 13-18.
Gelmi et al., "Solid substrate cultivation of *Gibberella fujikuroi* on an inert support"; Process Biochemistry. 2000, 35:1227-1233.
Jefferys, E.G., "The Gibberellin Fermentation", Adv. Appl. Biol. 1970, 13:283-315.
Kumar et al., "Microbial production of Gibberellins:state of the art," Adv. Appl. Microbiol., 1989, 34: 29-139.
Kumar et al., "Potential of fed-batch culture in solid state fermentation for production of gibberilic acid", Biotechnology Letters, 1987, 9(3): 179-182.
Kumar et al., "Batch and fed-batch solid-state fermentations: kinetics of cell growth, hydrolytic enzymes productin, and gibberellic acid production", Process Biochemistry, 1988, 23: 43-47.
Kumar et al., "Solid state fermentation : physical and nutritional factors influencing gibberellic acid production", Appl. Microbiol. Biotechnol. 1990, 34: 145-148.
Machado et al., "Kinetics of *Gibberella fujikuroi* growth and gibberellic acid production by solid-state fermentation in a packed-bed column bioreactor", Biotechnol. Prog., 2004, 20:1449-1453.
Booth, C., "The *Fusarium* problem: historical, economic and taxonomic aspects", in "The applied mycology of *Fusarium*", edited by Moss et al., Cambridge University Press, 1982, 1-12.
Pastrana et al., "Interactions affecting gibberellic acid production in solid-state culture: A factorial study", Enzyme and Microbial Technology, 1995, 17:784-790.
Prema et al., "Production of gibberellie acid by solid state fermentation: potential and feasibility.", Indian J. Microbiol., 1988, 28:1-2.
Puchooa et al., "A study on the use of carrot juice in the tissue culture of *Daucus carota*", African Journal of Biotechnology, 2004, 3(4): 248-252.
Qian et al, "Factors affecting gibberellic acid production by *Fusarium moniliforme* in solid-state cultivation on starch", World Journal of Microbiology & Biotechnology, 1994, 10:93-99.
Sharma et al. "Determination of gibberellins in fermentation broth produced by *Fusarium verticilliodes* MTCC 156 by high-performance liquid chromatography tandem mass spectrometry", Biotechnol. Appl. Biochem., 2004, 39, 83-88.
Tudzynski "Biosynthesis of gibberellins in *Gibberella fujikuroi*: biomolecular aspects", Appl. Microbiol. Biotechonol, 1999, 52: 298-310.

*Primary Examiner*—Herbert J. Lilling
(74) *Attorney, Agent, or Firm*—Foley & Lardner LLP (57) ABSTRACT

The present invention provides an improved process for the production of gibberellic acid ($GA_3$), achieving a yield over 225 g/kg of $GA_3$ with solid substrate fermentation, and over 15 g/L by submerged fermentation. The method also provides novel substrates, including the use of Jatropha seed cake. The present invention has in particular provided an improved, cost-effective process for the manufacture of $GA_3$, as the process has a surprisingly high yield of product, achieves the maximal yield in shorter time than other techniques, consumes less energy, and works with very inexpensive substrates. In all, the manufacturing costs are significantly reduced.

9 Claims, 4 Drawing Sheets

PROCESS FOR GIBBERELLIC ACID PRODUCTION WITH "FUSARIUM MONILIFORME" STRAINS

CROSS-REFERENCE TO RELATED APPLICATIONS

This application claims the benefit of Indian provisional application No. 1473/MUM/2006, filed on Sep. 15, 2006, the disclosure of which is incorporated by reference in its entirety.

FIELD OF THE INVENTION

The present invention relates to an improved process for the production of gibberellic acid by fermentation techniques. The present invention in particular relates to the production and optimization of gibberellic acid with strains of Fusarium moniliforme by submerged or solid state fermentation.

BACKGROUND OF THE INVENTION

Gibberellic acid ($GA_3$) is the most important gibberellin, a class of diterpenoid acids that function as plant growth regulators (Jefferys, E. G., *Adv. Appl. Biol.* 13:283-316 (1970)). $GA_3$ affects stem elongation, elimination of dormancy, flowering, sex expression, enzyme induction and leaf and fruit senescence. $GA_3$ is a high-value, industrially-important, biochemical with various applications in agriculture (L. M. Pastrana et al., "Interactions affecting gibberellic acid production in solid-state culture: A factorial study"; Enzyme and Microbial Technology 17:784-790 (1995), citing to Kumar, P. K. R., and Lonsane, B. K., *Appl. Microbiol. Biotechnol.* 34:145-148 (1990)). However, its high cost has restricted its use to premium crops (Jefferys, E. G., *Adv. Appl. Biol.* 13:283-316 (1970)).

$GA_3$ has been obtained by chemical synthesis, extraction from plants and by microbial fermentation. Stereospecific chemical synthesis involves multiple steps and the use of expensive reagents. To date, chemical synthesis is not economically competitive with fermentation techniques. Direct extraction of GAs from higher plants is not economically feasible due to extremely low concentration of GAs in plant tissue. A large number of bacteria, actinomycetes and yeast cultures have been reported to produce $GA_3$ or $GA_3$-like substances, but most do not produce $GA_3$ at commercially-feasible levels. Today, $GA_3$ is produced by fermentation, mostly from fungi.

Fermentation Methods $GA_3$ production in fungal culture includes liquid surface fermentation, submerged fermentation, and solid state fermentation.

Liquid Surface Fermentation (LSF)

Liquid surface fermentation (LSF), often referred to as surface fermentation, was employed in earlier years for the production of $GA_3$ but suffered from low yield (e.g. 3.3-9.2 g of crude powdered $GA_3$ from 130 liters of medium) problems with scalability, contamination and more, and was discontinued (P. K. R. Kumar and B. K. Lonsane, "Microbial production of Gibberellins: state of the art" in *Advances in Applied Microbiology.* 34: 29-140 (1989)).

Submerged Fermentation (SmF)

Currently, $GA_3$ is largely produced by submerged fermentation (SmF) of the fungus *Gibberella fujikuroi*. The fungus known as *Fusarium moniliforme* is also used; *F. moniliforme* is the anamorph (asexual stage) of *Gibberella fujikuroi*. $GA_3$ is also synthesized from several bacteria such as *Azotobacter*, and *Azospirillium* in culture medium and from wild strains of fungi such as *Sphaceloma* sp., *Phaeosphaeria* sp., and *Neurospora* sp.

The initial pH values generally employed by various workers are within the range 3.5-5.8, especially around pH 5.5. Id. pH was not usually controlled during fermentation and thus resulted in a final pH differing from the starting pH, with reports of the final pH of 3.9-5.2, 1.8-1.9, or even slight alkalinization. Id.

The effect of temperature on the production of $GA_3$ is dependent on the strain employed. The optimal temperatures reported for the production of $GA_3$ using *G. fujikuroi* or *F. moniliforme* include 25° C.; 28.5-29.5° C.; 30° C.; 34° C.; 29±0.5° C.; 27° C.; and 28° C. (See Id.)

Different workers have used a variety of carbon sources for the production of GAs, as reported by different authors. A combination of readily and slowly metabolizable carbon sources gave a higher yield of $GA_3$. Id. Use of molasses led to decreased but economically useful yields. Id. There was a 49% decrease in the yield of GAs with stearic acid as compared to sucrose. Use of dairy waste as carbon source resulted in 0.75 g $GA_3$/liter in 12 days. The production was completely inhibited by 1 ppm geraniol due to total inhibition of cell growth. A direct proportional relationship has been shown between the initial concentration of nitrogen supplied in the medium and the rate of product formation as well as the amount of metabolite produced. Id. See also Jefferys, E. G., *Adv. Appl. Biol.* 13:283-316 (1970)

Trace elements such as Fe, Cu, Mn, Zn, Al and Ca are required in the fermentative production of GAs. Id. Trace elements may be expressly added in excess or in combination, as in Raulin-Thom medium, or sufficient trace elements may be present as impurities in other ingredients of the fermentation medium. Id.

Other growth factors such as vitamins or Yeast extract may improve yield; while other heavy metals or the use of lines steel or stainless steel fermentation tanks can decrease yield. Id.

Various processes for production of $GA_3$ are described in U.S. Pat. Nos. 2,842,051, 2,865,812, 2,906,671, 2,906,673 and 3,021,261. U.S. Pat. No. 2,865,812 reported a yield of 630 mg/L in 664 hrs. Eleazar et al. ("Optimization of gibberellic acid production by immobilized *Gibberella fujikuroi* mycelium in fluidized bioreactors", Journal of Biotechnology, 76, 147-155 (2000)) reported yields by submerged fermentation as high as 2.862 g/L.

Solid Substrate Fermentation (SSF)

SSF (Solid Substrate Fermentation) is defined as any fermentation process performed on a non-soluble material that acts both as physical support and source of nutrients, in the absence of free flowing liquid. No free-moving water is present, but there is enough moisture present for the growth and metabolism of the microorganism. The low moisture content means that fermentation can only be carried out by a limited number of microorganisms, mainly yeasts and fungi, although some bacteria have been used. Work on the production of GAs using SSF technique was initiated in the early 1980s and the initial studies gave variable yields. No information was available on the economics of the process until early 1987. Three cases were examined wherein the yield of $GA_3$ under the SSF technique were 0.825, 1.05 and 1.54 g/kg of Dry Mouldy Bran. The yield of $GA_3$ in the fed-batch SSF Process was 1.54 g/kg of Dry Mouldy Bran as compared to 1.05 g/kg of Dry Mouldy Bran in the batch SSF process. Id. One group reported a yield of 3 g/kg by SSF (Bandelier, S., Renaud, R., and Durand, A., "Production of Gibberellic acid by Fed-batch solid state fermentation in an aseptic pilot-scale reactor", Process Biochemistry, 32:141-145 (1997)). B. Tudzynski ("Biosynthesis of gibberellins in *Gibberella fujikuroi*: biomolecular aspects"; Appl. Microbiol Biotechnol (1999) 52:298-310) reported that German Patent Number DD252000 also described processes for $GA_3$ by submerged fermentation, and reported yields of 8 g/kg.

Art-Known Fermentation Techniques Remain Expensive

Despite advances in fermentation technology, the cost of production of $GA_3$ has been a deterrent to its widespread use. Additional cost considerations include problems in the downstream processing and, given the potency of $GA_3$ to plants, removal and disposal of contaminated wastewater.

SUMMARY OF THE INVENTION

The inventors of the present invention have developed a process to manufacture $GA_3$ with *Fusarium moniliforme* by submerged and solid state fermentation and have been successful in obtaining yields over 15 g/L in submerged fermentation, and over 200 g/kg in solid state fermentation.

In one embodiment of the present invention, $GA_3$ is produced by solid state fermentation using various substrates such as wheat bran and Jatropha seed cake, to which mineral salts are added under high moisture content. The mixture is further inoculated with *F. moniliforme* and incubated for 10 days and the content of the mixture is analyzed for $GA_3$. $GA_3$ is isolated by adjusting the aqueous dilution of the mixture to acidic pH, and extracting using an organic solvent. The organic solvent is distilled and the $GA_3$ obtained is dissolved in ethanol.

In another embodiment of the present invention, $GA_3$ is produced by submerged fermentation by culturing *F. moniliforme* in Czapek-Dox media containing a carbon source, and incubating for 10 days.

The present invention has provided industrially-viable processes for the manufacture of $GA_3$ by fermentation processes such as solid-state fermentation or submerged fermentation. The present invention has in particular provided an improved, cost-effective process for the manufacture of $GA_3$, as the process has a surprisingly high yield of product, achieves the maximal yield in shorter time than other techniques, consumes less energy, and works with very inexpensive substrates. In all the manufacturing costs are significantly reduced.

In one embodiment, the present invention has focused on production and optimization of gibberellic acid by *Fusarium moniliforme* using various fermentation techniques.

The present disclosure provides $GA_3$ produced either by submerged or solid-state fermentation (SSF) technique. In certain embodiments, the submerged fermentation is carried out in reconstituted Czapek-Dox broth whereas solid-state fermentation is done on a humid solid matrix.

In another embodiment, the present invention relates to the use of microorganism belonging to the genus *Gibberella*, including *Gibberella fujikuroi* or *Fusarium moniliforme*.

Production of $GA_3$ is influenced by cultural conditions. In certain embodiments, high yields of $GA_3$ are obtained by varying factors, such as pH, temperature, incubation time, and other conditions such as optimization of the fermentation media.

In another embodiment, the present invention may use humid solid matrices substrates such as wheat bran or Jatropha seed cake.

In another embodiment, the production process of $GA_3$ by submerged fermentation involves incubating the fungi in liquid media containing various minerals, sodium nitrate as the nitrogen source, and sucrose as the carbon source.

In another embodiment, the present invention has optimized the pH conditions for submerged fermentation. The process of the present invention provides an optimal pH in the range of 5-8. In one embodiment, the pH is pH 7.0

In another embodiment, the present invention has optimized the temperature conditions for submerged fermentation. The present invention provides an optimal temperature ranging between 25° C. (room temperature) to 37° C. In one embodiment, the temperature is 30° C.

In another embodiment, the present invention has optimized the carbon source for submerged fermentation. In one embodiment, the carbon source is sucrose or glucose.

In another embodiment, the present invention has optimized the media for submerged fermentation. In one embodiment, the medium is reconstituted Czapek-Dox medium.

In still another embodiment, the present invention provides a process for production of $GA_3$ by solid-state fermentation. In one embodiment, this involves growing fungi on wheat bran supplemented with a mineral salts solution.

In the case of $GA_3$ production in SSF, factors that affect yield include temperature, pH, moisture, substrate particle size, light, autoclave timing, incubation period, amount and age of inoculum.

$GA_3$ was produced by submerged or solid-state fermentation (by free or immobilized cells, respectively). We observed that the yield from solid-state fermentation was as high as 39 g/kg using wheat bran as a substrate, and 237.2 g/kg, when using of Jatropha seed cake as substrate. To the best knowledge of the inventors, the $GA_3$ yields of the present invention are higher than any reported, by any mode of fermentation. For example, only one previous report provides a yield as high as 19.3 g/kg of $GA_3$, which was obtained using starch (corn flour) as substrate (Gelmi et al. ("Solid substrate cultivation of *Gibberella fujikuroi* on an inert support"; *Process Biochemistry*. 35: 1227-1233 (2000), citing to Qian et al., (*World J. Microbiol Biotechnol.* 10:93-98, (1994))).

A comparison of the present invention with conventional methods was performed. $GA_3$ produced by the present invention by submerged is greater than 3-fold higher than the highest yield reported in the literature; and by solid-state fermentation greater than 10-fold higher. The present process has demonstrated a yield greater than 15 g/L by submerged fermentation, and greater than 225 g/kg by solid state fermentation.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

DETAILED DESCRIPTION OF THE INVENTION

Definitions

As used herein the term $GA_3$ or gibberellic acid refers to gibberellic acid with the molecular weight of 346.38 g/mol.

As used herein the term "solid state fermentation (SSF)" includes a process wherein the microbial growth and formation of product on and inside a humid solid matrix is in the absence of free water. This is also known as "solid substrate fermentation.

As used herein the term "submerged fermentation" includes a process wherein microbe is grown in a liquid medium and the product is secreted into the media.

The mineral salts solution used in the present invention comprises copper sulphate, ferric chloride and zinc sulphate.

Czapek-Dox (Himedia-M076) media contains the following components (per liter)

| | |
|---|---|
| sucrose | 30 g |
| sodium nitrate | 3 g |
| dipotassium phosphate | 1 g |
| magnesium sulphate | 0.5 g |
| potassium chloride | 0.5 g |
| ferrous sulphate | 0.01 g |
| distilled water | 1000 ml |

In one embodiment, the Czapek-Dox media is reconstituted rather than commercially purchased. Reconstituted Czapek-Dox media is prepared by adding all components individually in water at the same concentrations as that of commercially available media.

One substrate used in the present invention is Jatropha seed cake. Jatropha is grown for its oil, which is extracted after crushing the seeds. Typically, seeds are ground to uniform sized particles and oil is extracted by Soxhlet extraction using Hexane as a solvent. Jatropha seed cake "with oil" means that the seeds have been crushed, but before the oil has been extracted. Seed cake "without oil" refers to seed cake left over after oil extraction, from which more than about 95% of the oil has been removed.

Solid State Fermentation

The present disclosure provides an improved process for the production of $GA_3$ either by submerged fermentation or solid state fermentation.

In one embodiment, $GA_3$ production via solid state fermentation comprises the following steps:
  a) Preparation of solid substrate mixture;
  b) Inoculation with *F. moniliforme* culture;
  c) Incubation;
  d) Extraction of $GA_3$; and
  e) Purification.

In certain embodiments, the solid-state substrate used in the present invention is wheat bran (50 g) or Jatropha seed cake (5 g) to which is added mineral salt solutions (30 ml and 8 ml, respectively) under high moisture content and then autoclaved in the flasks. In one embodiment, autoclaved substrate is inoculated with *F. moniliforme* culture in Czapek-Dox broth.

In one embodiment, incubation of the substrate is done at temperatures ranging between 25-37° C. and analyzed for $GA_3$ content, at periodic intervals, using a spectrophotometric method (Berrios et al. (Spectrophotometric method for determining Gibberellic acid in fermentation broths. Biotechnology Letters, 26: 67-70 (2004)), high-pressure liquid chromatography (HPLC) and/or thin-layer chromatography (TLC). In TLC the culture filtrate obtained after fermentation was subjected to extraction and purification as described above. The residue obtained was dissolved in ethanol and separated by thin layer chromatography using isopropanol-ammonia-water (10:1:1, v/v/v) as mobile phase. The plates were sprayed with 3% sulphuric acid in methanol containing 50 mg ferric chloride and heated in an oven at 80° C. for 10 min. GAs fluoresce and appear as greenish spot under UV light, allowing their detection. (D. Puchooa and R. Ramburn; "A study on the use of carrot juice in the tissue culture of *Daucus carota*: African Journal of Biotechnology, Vol. 3(4), pp. 248-252, April-2004).

The inventors of the present invention extracted $GA_3$ by diluting the above mixture with water, and acidification with concentrated HCl, to pH 2.5. To 5 ml of broth, 60 ml of methanol:chloroform:2 N ammonium hydroxide in the ratio of 12:5:3 and 25 ml of distilled water was added. The mixture was shaken well in a separating funnel. The bottom chloroform layer was removed and methanol in the upper aqueous layer was evaporated. After adjusting the pH of the remaining solution to 2.5, the solution was extracted thrice with 15 ml of ethyl acetate each time. The ethyl acetate phase was collected and evaporated to dryness. The dried material was dissolved in 5 ml of ethanol and the amount of $GA_3$ was determined. To a 1 ml aliquot of the sample in ethanol, 8 ml of 3.75N HCl was added and O.D. was measured at 254 nm after 2 min., following the protocol of Berrios et al. (2004).

Various substrates have been used for solid state fermentation in the literature. Machado et al. reported a yield of 0.925 g of $GA_3$/kg of biomass using coffee husk or cassava bagasse as a medium (Machado, C. M. M., Oishi, B. O., Pandey, A., and Soccol, C. R., *Biotechnol. Prog.* 20:449-1453 (2004)). Gelmi et al. ("Solid substrate cultivation of *Gibberella fujikuroi* on an inert support"; *Process Biochemistry.* 35: 1227-1233 (2000)) reported that Qian et al., (*World J. Microbiol. Biotechnol.* 10:93-98, (1994)) achieved a yield of 19.3 g $GA_3$/kg of dry fermented substrate after 18 days of cultivation using corn flour as a substrate (although Gelmi suggested that the yield was actually less, when taking into account degradation of the substrate).

Gelmi, ibid. also reported that other workers achieved yields of 3.8 g $GA_3$/kg vermiculite and of 6.8 g $GA_3$/kg initial dry mass over 190 h, using a wheat bran culture medium. A yield of 8 g/kg of $GA_3$ was obtained on rice as a substrate (German Patent Number DD 252000). Prema et al., *Indian J. Microbiol.* 28:1-2 (1988)) reported very low yields of $GA_3$ (1.14 g/kg) and Kumar, P. K. R., and Lonsane, B. K., *Appl. Microbiol. Biotechnol.* 34:145-148 (1990), reported 1.2 g/kg of $GA_3$ using wheat bran as a medium.

The present invention has obtained $GA_3$ using wheat bran, and using Jatropha seed cake with oil and without oil. The present invention has found that the $GA_3$ yields were as high as 237.2 g/kg using Jatropha seed cake with oil on the 6th day, which is more than ten fold higher than the previously reported possible yield of 19.3 g/kg (Gelmi, ibid.). The $GA_3$ yield obtained by using Jatropha seed cake as a substrate was also five fold higher than that obtained by wheat bran under the present optimized conditions (see Examples).

In certain embodiments, the yield of $GA_3$ in the present invention is further improved by having a higher initial moisture level of 60% and a lower incubation temperature of 23° C. as compared to moisture level of 50% at 28° C. or 30° C., as reported in Prema et al., *Indian J. Microbiol*. 28:1-2 (1988), or Pastrana et al., Enzyme and Microbial Technology, 17:784-790, 1995 (1995). There does exist one report wherein the temperature was decreased from 28° C. to 22° C. as the fermentation progressed. However, the yield of $GA_3$ was only 3 g/kg (Bandelier et al., *Process Bioche*. Vol. 32 2:141-145 (1997)).

Submerged Fermentation

In one embodiment, the present invention provides a process for submerged fermentation which comprises the following steps:
1. Preparation of the inoculum;
2. Incubation in medium containing sugars;
3. Extraction of $GA_3$; and
4. Purification.

In one embodiment, the inoculum is prepared by culturing and maintaining *F. moniliforme* in Czapek-Dox broth medium, in the presence of a carbon source, such as sucrose or glucose.

In the present invention, various conditions such as pH, temperature, carbon source, and the media may be optimized for high yield.

One group has previously reported a yield of $GA_3$ of 5 g/L by submerged fermentation, using a fed-batch cultivation mode under conditions of nitrogen limitation using genetically improved strains (P. K. R. Kumar and B. K. Lonsane, "Microbial production of Gibberellins: state of the art" in *Advances in Applied Microbiology*. 34: 29-140 (1989)).

General Comments

The following examples are included to demonstrate certain exemplary embodiments of the invention. It should be appreciated by those of skill in the art that the techniques disclosed in the examples which follow represent techniques discovered by the inventor to function well in the practice of the invention, and thus can be considered to constitute exemplary modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Organism

*Fusarium moniliforme* NCIM 1100 was obtained from National Collection of Industrial Microorganisms, Pune, India. The strain was cultured and maintained on sterile potato dextrose agar (PDA) slants. Unless otherwise indicated, the media used for production of gibberellic acid was Czapek-Dox (Himedia-M076) and the culture was incubated at 30° C. for 10 days on as shaker incubator at 150 rpm.

Example 2

Solid Substrate Fermentation with Wheat Bran

To 50 g wheat bran, 30 ml of a mineral salts solution (copper sulphate, 0.007 g; ferric chloride, 0.007 g; and zinc sulphate, 0.007 g, dissolved in 1 liter of 0.2N HCl) was added and mixed well. The mixture was then distributed equally into five flasks and sterilized at 15 PSI for 30 min. The autoclaved wheat bran in each flask was inoculated with 10 ml of 6 days old *F. moniliforme* culture from Czapek-Dox broth, mixed thoroughly and were incubated at 30° C. for 10 days at a 45° angle. Yield was determined by the method of Berrios et al., as described below.

Yield of $GA_3$ from wheat bran under SSF, over time.

| Days of incubation | $GA_3$ concentration (g/kg) in solid substrate fermentation (wheat bran) |
|---|---|
| 5 | 29 |
| 6 | 32 |
| 7 | 33 |
| 8 | 34 |
| 9 | 39 |
| 10 | 39.4 |

Example 3

Analytical Procedures $GA_3$ was determined spectrophotometrically by the method described by Berrios et al. (Biotechnology Letters 26: 67-70, (2004)) at 254 nm. $GA_3$ was also determined by HPLC at 206 nm using a C18 column with methanol:water (3:1) as the mobile phase at 1 ml/min flow rate, as described by Sharma et al. (Biotechnol. Appl. Biochem., 39, 83-88 (2004)). The retention time of $GA_3$ is 3 minutes under these conditions.

$GA_3$ was also detected by TLC as described by Puchooa et al. (African Journal of Biotechnology, 3(4): 248-252 (2004)). The culture filtrate obtained after fermentation was subjected to extraction and purification as described below. The obtained residue was dissolved in ethanol and separated by TLC using isopropanol-ammonia-water (10:1:1, v/v/v) as mobile phase. The plates were sprayed with 3% sulphuric acid in methanol containing 50 mg ferric chloride and heated in an oven at 80° C. for 10 min. $GA_3$ fluoresce and appear as a greenish spot under UV light.

Example 4

Extraction of $GA_3$ from the Wheat Bran Solid Substrate $GA_3$ was extracted from the solid substrate by adding 100 ml of distilled water to moldy bran in each flask and were kept on shaking incubator at 150 rpm for 2 hrs. The slurry from each flask was filtered through muslin cloth and the volume of the filtrate was made to 100 ml. Filtrate was centrifuged at 10000 rpm for 10 min at 28° C. Supernatant was collected and analyzed for $GA_3$ concentration spectrophotometrically.

Example 5

Purification of $GA_3$

Isolation of $GA_3$ from the solid substrate extract was done by the method described in Ergun et al. (Turk J. Bot., 26: 13-18 (2002)). Briefly, to 5 ml of the water extract from the solid substrate, 60 ml of methanol:chloroform:2 N ammonium hydroxide in the ratio of 12:5:3 and 25 ml of distilled water was added. The mixture was shaken well in a separating funnel. The bottom, chloroform, layer was removed and methanol in the upper aqueous layer was evaporated. After adjusting the pH of the remaining solution to 2.5 with concentrated HCl the solution was extracted thrice with 15 ml of ethyl acetate. The ethyl acetate phase was collected and evaporated to dryness. The dried material was dissolved in 5 ml of ethanol and $GA_3$ was determined, using the protocol of Berrios et al. This method of purification may also be adapted to $GA_3$ from submerged fermentation.

Example 6

Solid Substrate Fermentation with Jatropha Seed Cake

Jatropha seed cake, one of cheapest substrates available, was employed as the substrate for the production of $GA_3$. Production of gibberellic acid using Jatropha as the substrate has never been previously reported. Both Jatropha seed cake with oil and without oil were used as the substrate. Five flasks (5 g of Jatropha, 8 ml of MSS (copper sulphate 0.007 g; ferric chloride 0.007 g; zinc sulphate: 0.007 g; dissolved in 1 liter of 0.2N HCl) and 3.5 ml of inoculum)) were inoculated with 3.5 ml of four day old inoculum of $F.$ $moniliforme$, and were incubated at room temperature. Growth was observed within 24 hours of inoculation. Maximum yield was obtained on the $6^{th}$ day of incubation and the yield was found to decrease on the $8^{th}$ and $10^{th}$ day.

Figure 1:
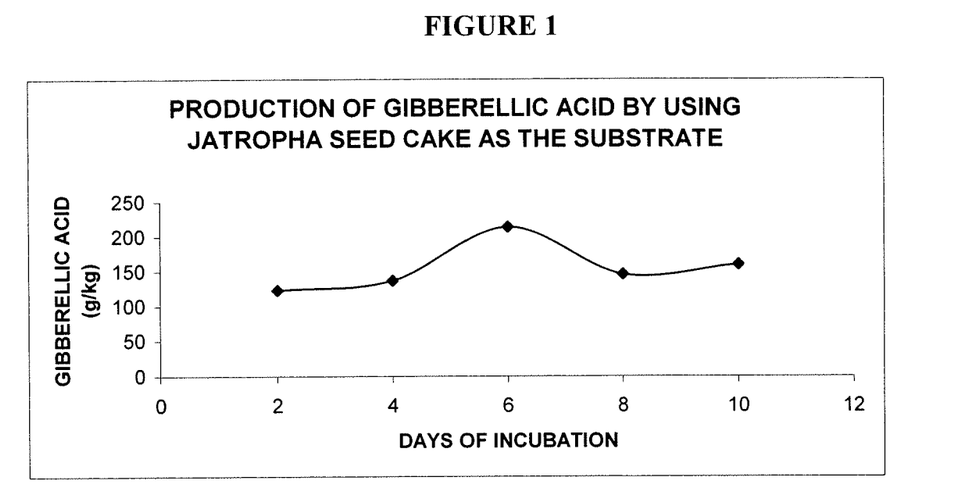
FIG. 1: Production of $GA_3$ production (g/kg) by *F. moniliforme* in SSF using Jatropha seed cake as the substrate.

As depicted in FIG. 1, the maximum yield of $GA_3$ obtained was 237.2 g/kg by SSF. This is so far the best-reported yield of $GA_3$ obtained by SSF. The $GA_3$ extracted from the SSF migrated on TLC as a single spot similar to the standard and showed an $R_f$ value of 0.74, consistent with $GA_3$.

Example 7

Production of $GA_3$ in Jatropha Seed Cake without Oil

The production of gibberellic acid was determined every 48 hours. Five flasks (5 g of Jatropha seed cake without oil, 8 ml of mineral salts solution MSS and 3.5 ml of inoculum) were inoculated with 3.5 ml of four day old inoculum ($F.$ $moniliforme$) and was incubated at room temperature. Maximum yield was obtained on the $6^{th}$ day of incubation and the yield was found to decrease on the $8^{th}$ and $10^{th}$ day.

| Days of incubation | $GA_3$ Concentration g/kg |
| --- | --- |
| 2 | 122 |
| 4 | 136 |
| 6 | 213 |
| 8 | 145 |
| 10 | 159 |

Example 8

Comparison of Yield from Jatropha Seed Cake with Oil and without Oil

Gibberellic acid was produced by using Jatropha seed cake with oil and without oil as the substrates. A very slight difference was observed in the yield, however yield from Jatropha seed cake with oil (149.72 g/kg) was found to be slightly higher than the yield obtained from Jatropha seed cake without oil (140.22 g/kg) on day 10 after inoculation.

Example 9

Figure 2:
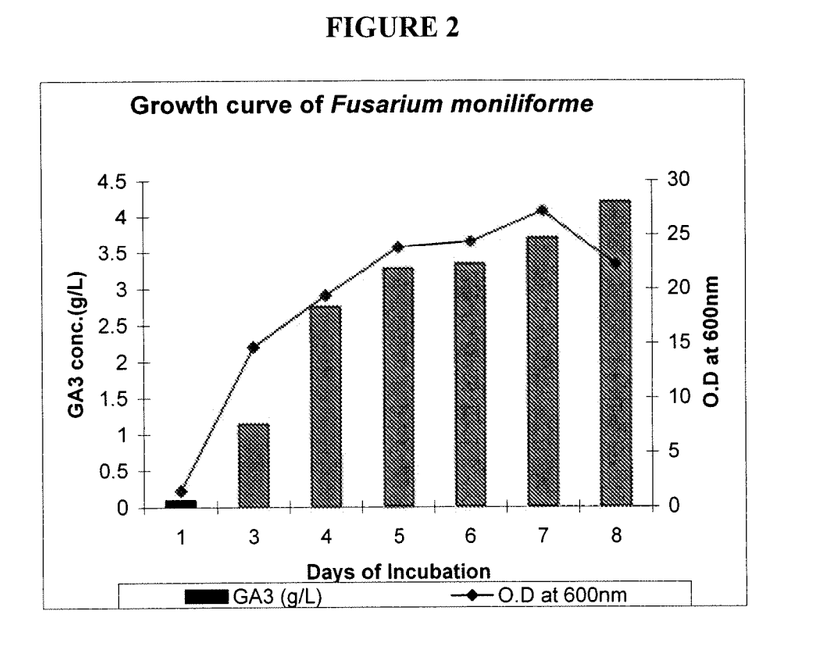
FIG. 2: Illustrates $GA_3$ production in g/L and biomass, as determined by OD at 600 nm, for *Fusarium moniliforme* grown by submerged fermentation in commercial Czapek-Dox broth.

Submerged Fermentation $Fusarium$ $moniliforme$ culture was inoculated from PDA slants into 250 ml of commercial Czapek-Dox broth at an initial pH of 7.0, and incubated at 30° C. for 10 days on a shaking incubator at 150 rpm. Cell growth was monitored by collecting 1 ml of culture from fermented broth every 24 h, and centrifuged at 13200 rpm for 10 min. The supernatant was used for $GA_3$ estimation, and the pellet, washed thrice with saline, was used for determining cell growth. The growth and $GA_3$ production patterns of $F.$ $moniliforme$ culture in Czapek-Dox broth is shown in FIG. 2.

After an initial lag, there was an exponential increase in growth. This log phase continued up to 5 days before reaching a plateau indicating the commencement of stationary phase. Production of GA was found to start increasing during the late exponential phase (5 days) and extending well into the stationary phase before reaching a plateau (FIG. 2). Under these conditions, the yield of $GA_3$ reached the highest on the $8^{th}$ day.

| Days of Incubation | $F.$ $moniliforme$ inoculum | |
| --- | --- | --- |
| | $GA_3$(g/L) | Biomass |
| 1 | 0.09 | 1.50 |
| 2 | — | — |
| 3 | 1.92 | 14.70 |
| 4 | 2.76 | 19.44 |
| 5 | 3.29 | 23.84 |
| 6 | 3.35 | 24.36 |
| 7 | 3.71 | 27.20 |
| 8 | 4.21 | 22.24 |
| 9 | — | — |
| 10 | 4.02 | 24.56 |

Example 10

Optimization of pH in Submerged Fermentation

Figure 3:
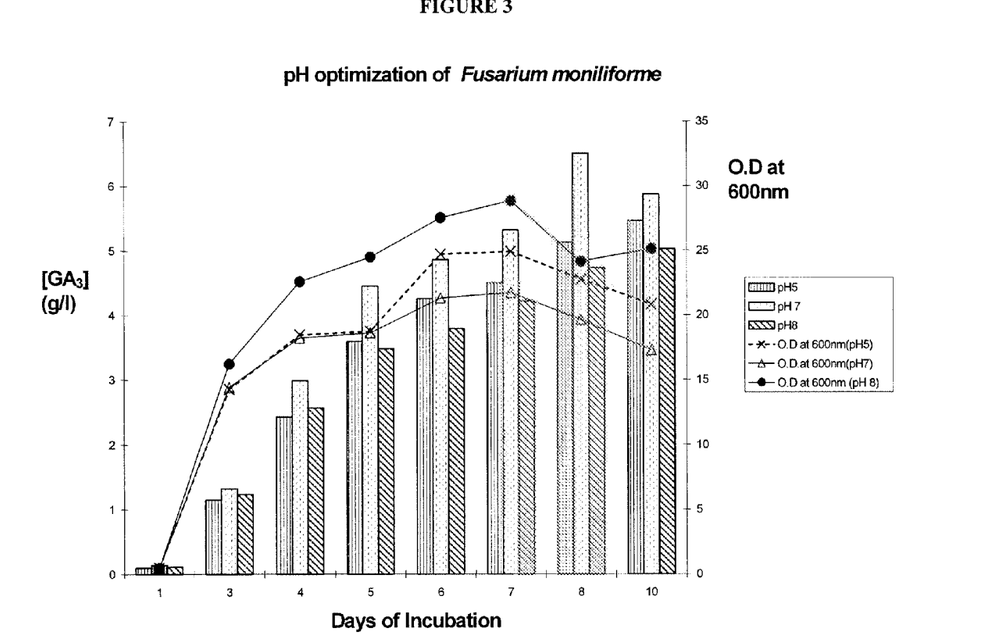
FIG. 3: Illustrates the effect of pH on $GA_3$ production (g/L) and biomass (OD at 600 nm) by *F. moniliforme* in submerged fermentation in commercial Czapek-Dox broth.

Optimization studies were carried out to increase the yield of $GA_3$. To determine the optimal pH for the growth and production of gibberellic acid, $Fusarium$ $moniliforme$ culture was inoculated into 100 ml of broth in 250 ml flasks, with flasks having different initial pH values (5, 7 and 8). The cultures were incubated at 30° C. for 10 days on a shaking incubator at 150 rpm. Sampling of 1 ml of broth was done every 24 h throughout the incubation period, to determine cell growth and $GA_3$ concentration. Initial pH did not have any significant effect on the $GA_3$ yield (FIG. 3) although the highest yield (6.5 g/L) was obtained at an initial pH of 7.0.

| Days of Incubation | pH 5 $GA_3$(g/L) | pH 7 $GA_3$(g/L) | pH 8 $GA_3$(g/L) |
| --- | --- | --- | --- |
| 1 | 0.10 | 0.14 | 0.11 |
| 2 | — | — | — |
| 3 | 1.15 | 1.32 | 1.24 |
| 4 | 2.43 | 2.99 | 2.57 |
| 5 | 3.59 | 4.45 | 3.48 |
| 6 | 4.25 | 4.86 | 3.79 |
| 7 | 4.50 | 5.31 | 4.22 |

-continued

| Days of Incubation | pH 5 GA₃(g/L) | pH 7 GA₃(g/L) | pH 8 GA₃(g/L) |
|---|---|---|---|
| 8 | 5.10 | 6.50 | 4.73 |
| 9 | — | — | — |
| 10 | 5.46 | 5.87 | 5.02 |

Example 11

Optimization of Temperature in Submerged Fermentation

Figure 4:
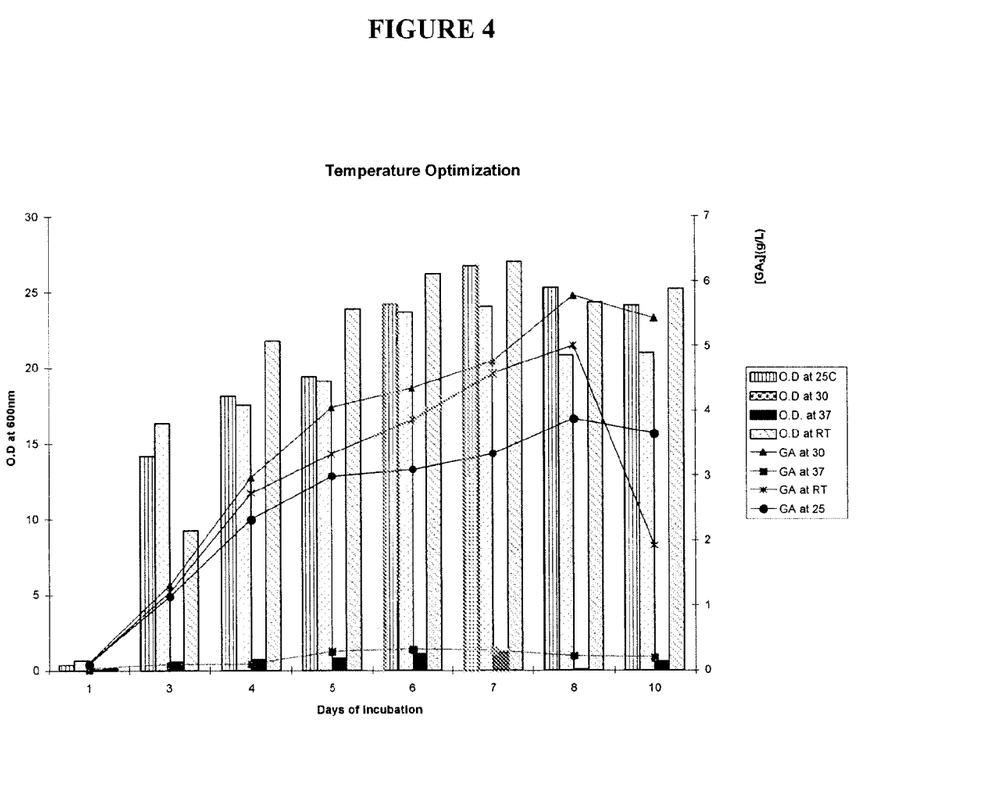
FIG. 4: Illustrates the effect of temperature on $GA_3$ production by *F. moniliforme* in submerged fermentation in Czapek-Dox broth.

The optimal temperature for the growth and production of gibberellic acid by *Fusarium moniliforme* was evaluated. The *F. moniliforme* culture was inoculated into four different Czapek-Dox broth flasks, which were incubated at different temperatures (25° C., 30° C., 37° C., and room temperature of 23-25° C.) for 10 days on a shaking incubator at 150 rpm. Sampling was done after every 24 hrs for determination of cell growth and $GA_3$ concentration. Incubation at 30° C. was the optimal condition for maximizing the production of $GA_3$ (FIG. 4).

| Days of Incubation | 25° C. GA₃(g/L) | 30° C. GA₃(g/L) | 37° C. GA₃(g/L) | 23° C. GA₃(g/L) |
|---|---|---|---|---|
| 1 | 0.10 | 0.11 | 0.024 | 0.10 |
| 2 | — | — | — | — |
| 3 | 1.14 | 1.32 | 0.092 | 1.21 |
| 4 | 2.33 | 2.97 | 0.10 | 2.73 |
| 5 | 3.0 | 4.06 | 0.29 | 3.33 |
| 6 | 3.10 | 4.34 | 0.33 | 3.86 |
| 7 | 3.34 | 4.76 | 0.32 | 4.57 |
| 8 | 3.88 | 5.77 | 0.23 | 5.01 |
| 9 | — | — | — | — |
| 10 | 3.65 | 5.42 | 0.2 | 1.92 |

Example 12

Optimization of Carbon Source in Submerged Fermentation

Figure 5:
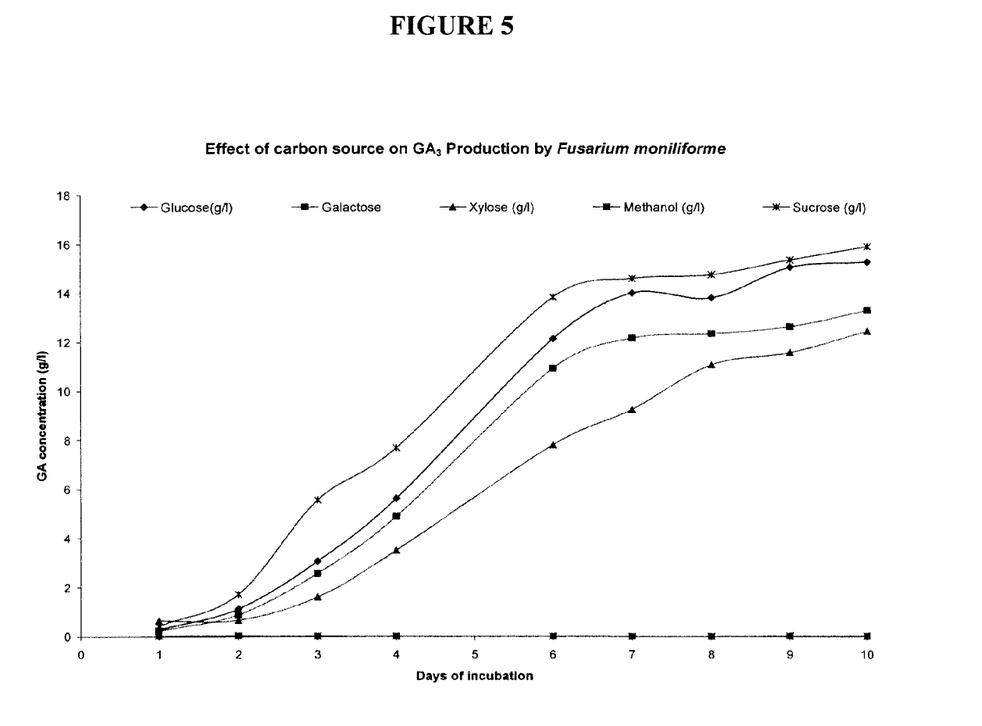
FIG. 5: Illustrates the effect of carbon source on $GA_3$ production by *F. moniliforme* in submerged fermentation in Czapek-Dox broth. No growth was observed when acetic acid was used as the carbon source.

To determine the carbon source, which gives optimal yield of $GA_3$ production, the following carbon sources were used: sucrose, glucose, galactose, xylose, glacial acetic acid and methanol. *Fusarium* culture was inoculated into reconstituted Czapek-Dox medium containing the aforementioned carbon sources and incubated at 30° C. for 10 days on a shaking incubator at 150 rpm. Sampling was done every 24 hrs throughout the incubation period for determining the cell growth and the $GA_3$ concentration. Sucrose and glucose were found to be the best source of carbon giving a yield of over 15 g/L (FIG. 5). Galactose and xylose also gave yields higher than 8 g/L.

| Days of Incubation | Glucose | Galactose | Xylose | Methanol | Glacial Acetic acid | Sucrose |
|---|---|---|---|---|---|---|
| 1 | 0.28 | 0.23 | 0.64 | 0.026 | No Growth | 0.43 |
| 2 | 1.12 | 0.89 | 0.66 | 0.028 | No Growth | 1.72 |
| 3 | 3.07 | 2.57 | 1.61 | 0.018 | No Growth | 5.57 |
| 4 | 5.63 | 4.89 | 3.51 | 0.015 | No Growth | 7.69 |
| 6 | 12.14 | 10.93 | 7.81 | 0.014 | No Growth | 13.85 |
| 7 | 14.02 | 12.17 | 9.25 | 0.001 | No Growth | 14.6 |
| 8 | 13.82 | 12.35 | 11.08 | 0.0 | No Growth | 14.76 |
| 9 | 15.07 | 12.64 | 11.58 | 0.023 | No Growth | 15.37 |
| 10 | 15.28 | 13.3 | 12.45 | 0.018 | No Growth | 15.91 |

Example 13

Optimization of Submerged Fermentation

A *Fusarium moniliforme* culture was inoculated into reconstituted Czapek-Dox medium, followed by incubation at 30° C. at an initial pH of 7.0, using sucrose as the carbon source, and was incubated for 10 days on a shaking incubator maintained at 150 rpm. Sampling was done every 24 h throughout the incubation period for determining the cell growth and the $GA_3$ concentration. As shown in the following table, the yield reached 15.9 g/L at 10 days.

| Days of incubation | GA₃(g/L) |
|---|---|
| 1 | 0.43 |
| 2 | 1.72 |
| 3 | 5.57 |
| 4 | 7.70 |
| 5 | — |
| 6 | 13.85 |
| 7 | 14.60 |
| 8 | 14.76 |
| 9 | 15.37 |
| 10 | 15.91 |

Discussion: Yield from Submerged Fermentation and Solid Substrate Fermentation.

The $GA_3$ yield was determined in both submerged fermentation and solid substrate fermentation. The yield obtained from solid substrate fermentation reached as high as 237.2 g/kg when using Jatropha seed cake as a substrate, and as high as 39.4 g/kg when using wheat bran as a substrate. The yield obtained from submerged fermentation reached as high as 15.9 g/L.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention.

More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A process for producing gibberellic acid ($GA_3$) comprising:
   (a) growing *Fusarium moniliforme* by solid-state fermentation in the presence of Jatropha seed cake as a substrate; and
   (b) obtaining gibberellic acid;
   wherein the yield of gibberellic acid is at least 30 g gibberellic acid/kg of substrate.

2. The process of claim 1, wherein the yield of gibberellic acid is at least 100 g gibberellic acid/kg of substrate.

3. The process of claim 1, wherein the yield of gibberellic acid is at least 200 g gibberellic acid/kg of substrate.

4. The process of claim 1, wherein the Jatropha seed cake substrate is with oil.

5. The process of claim 1, wherein the Jatropha seed cake substrate is without oil.

6. The process of claim 1, wherein the solid-state fermentation is carried out in the presence of a mineral salt solution.

7. The process of claim 1, wherein the solid-state fermentation is stopped after 6 days.

8. The process of claim 1, wherein initial moisture level is 60%, and the temperature is 23° C. in step (a).

9. The process of claim 1, wherein the process further comprises inoculating *Fusarium moniliforme* in the presence of the Jatropha seed cake substrate and a mineral salt solution comprising copper sulfate, ferric chloride and zinc sulphate.

* * * * *